United States Patent
Adams et al.

(10) Patent No.: US 6,645,146 B1
(45) Date of Patent: Nov. 11, 2003

(54) METHOD AND APPARATUS FOR HARMONIC IMAGING USING MULTIPLE TRANSMISSIONS

(75) Inventors: Qian Zhang Adams, New Berlin, WI (US); Satchi Panda, Greenfield, WI (US); Richard Yung Chiao, Menomonee Falls, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/285,902

(22) Filed: Nov. 1, 2002

(51) Int. Cl.[7] ................................................. A61B 8/00
(52) U.S. Cl. ..................................................... 600/443
(58) Field of Search .................................. 600/443, 447, 600/448, 449, 455, 437, 446, 456, 457

(56) References Cited

U.S. PATENT DOCUMENTS

| | | | | |
|---|---|---|---|---|
| 5,410,516 A | * | 4/1995 | Uhlendorf et al. | ............. 367/7 |
| 6,132,374 A | | 10/2000 | Hossack et al. | |
| 6,146,328 A | * | 11/2000 | Chiao et al. | ................. 600/443 |

* cited by examiner

Primary Examiner—Francis J. Jaworski
Assistant Examiner—Maulin Patel
(74) Attorney, Agent, or Firm—Joseph S. Heino; Carl B. Horton (57) ABSTRACT

A method and apparatus for improving the penetration of the harmonic imaging while preserving the image uniformity by using signals from a similar frequency band to form a composite image. A near field image uses primarily tissue generated harmonic signal associated with a first transmitting event that has a center frequency of $f_1$. Such tissue generated harmonic signal has a frequency band centered on $2f_1$. In the far field, fundamental echo signals from the second transmitting event that has a center frequency of $f_2$ are primarily use. Since the center frequency $f_2$ in the transmitting event is close to $2f_1$ and there is a significant overlap in frequency band between signals extracted from the first transmitting event and signals extracted from the second transmitting event, a composite image formed from these signals has similar speckle size across the whole image. The extracted signal from the second transmitting event is a fundamental component of the received echo and such signal has much larger amplitude than the tissue generated harmonic signal from the first transmitting event. Adding the fundamental signal from the second transmitting event in the far field improves the penetration of the harmonic imaging without sacrificing image uniformity.

24 Claims, 8 Drawing Sheets

METHOD AND APPARATUS FOR HARMONIC IMAGING USING MULTIPLE TRANSMISSIONS

FIELD OF THE INVENTION

This invention relates generally to ultrasound imaging systems. More particularly, it relates to a method and apparatus for using multiple transmissions to blend a fundamental signal into a harmonic image to improve the penetration of harmonic imaging without sacrificing image uniformity.

BACKGROUND OF THE INVENTION

Conventional ultrasound imaging systems comprise an array of ultrasonic transducer elements that transmit an ultrasound beam and then receive a reflected beam from the object being studied. This operation comprises a series of measurements in which a focused ultrasonic wave is transmitted, the system switches to receive mode after a short time interval, and the reflected ultrasonic wave is received, beamformed and processed for display. Transmission and reception are typically focused in the same direction during each measurement to acquire data from a series of points along an acoustic beam, also known as a scan line. The receiver is dynamically focused at a succession of ranges along the scan line as the reflected ultrasonic waves are received.

For ultrasound imaging, the array typically has a multiplicity of transducer elements arranged in a line and driven by separate voltages under separate time delay. By controlling the time delay (or phase) and amplitude of the voltages applied to the individual transducer elements, a net ultrasonic wave that travels along a preferred vector direction and is focused at a selected point along the beam can be formed. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. In the case of a steered array, by changing the time delays and amplitudes of the applied voltages, the beam with its focal point can be moved in a plane to scan the object. In the case of a linear array, a focused beam directed normal to the array is scanned across the object by translating the aperture across the array from one firing to the next.

The same principles apply when an ultrasonic transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delays (and/or phase shifts) and gains to the signal from each receiving transducer element.

An ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more of the receive—beamformers coherently sum the energy received by each channel, with dynamically changing phase rotation or delays, to produce peak sensitivity along the desired scan lines at ranges proportional to the elapsed time. The resulting focused sensitivity pattern is the result of the directivity of the associated transmit and receive beam pair.

The output signals of the beamformer channels are coherently summed to form a respective pixel intensity value for each sample volume in the object region or volume of interest. These pixel intensity values are log-compressed, scan-converted and then displayed as an image of the anatomy being scanned.

In the prior art, signals used to form an image reside in either a first frequency band or in a second frequency band. The first frequency band comprises the fundamental band and the second frequency band comprises a harmonic of the fundamental frequency band. The second frequency band substantially excludes the first frequency band. A composite image is formed by signals from the second frequency band in the near field and by signals from the first frequency band in the far field. While such method can improve the penetration of the harmonic imaging, it achieves this at the expense of the image uniformity. The image speckle size associated with the first frequency band is usually much bigger than that associated with the second frequency band. As a result, the composite image has a smaller speckle size in the near field and larger speckle size in the far field, which leads to the degradation in the image uniformity.

SUMMARY OF THE INVENTION

The current invention is a method and an apparatus for improving the penetration of the harmonic imaging while preserving the image uniformity. It achieves this by using signals from a similar frequency band to form a composite image. More specifically, a near field image uses primarily tissue generated harmonic signal associated with the first transmitting event that has a center frequency of $f_1$. Such tissue generated harmonic signal has a frequency band centered on $2f_1$. In the far field, fundamental echo signals from the second transmitting event that has a center frequency of $f_2$ are primarily used. Since the center frequency $f_2$ in the second transmitting event is close to $2f_1$, and there is a significant overlap in frequency band between signals extracted from the first transmitting event and signals extracted from the second transmitting event, a composite image formed from these signals has similar speckle size across the whole image. Because the extracted signal from the second transmitting event is a fundamental component of the received echo, such signal has much larger amplitude than the tissue generated harmonic signal from the first transmitting event. Therefore, adding the fundamental signal from the second transmitting event in the far field improves the penetration of the harmonic imaging without sacrificing the image uniformity.

In short, the method and apparatus of the present invention blends a fundamental signal into a harmonic image to improve penetration of the harmonic imaging. The blending is done in such a way that penetration of a harmonic image is improved without sacrificing the image uniformity. The foregoing and other features of the method and apparatus of the present invention will be apparent from the detailed description that follows.

DETAILED DESCRIPTION OF THE PREFERRED EMBODIMENTS

Figure 1:
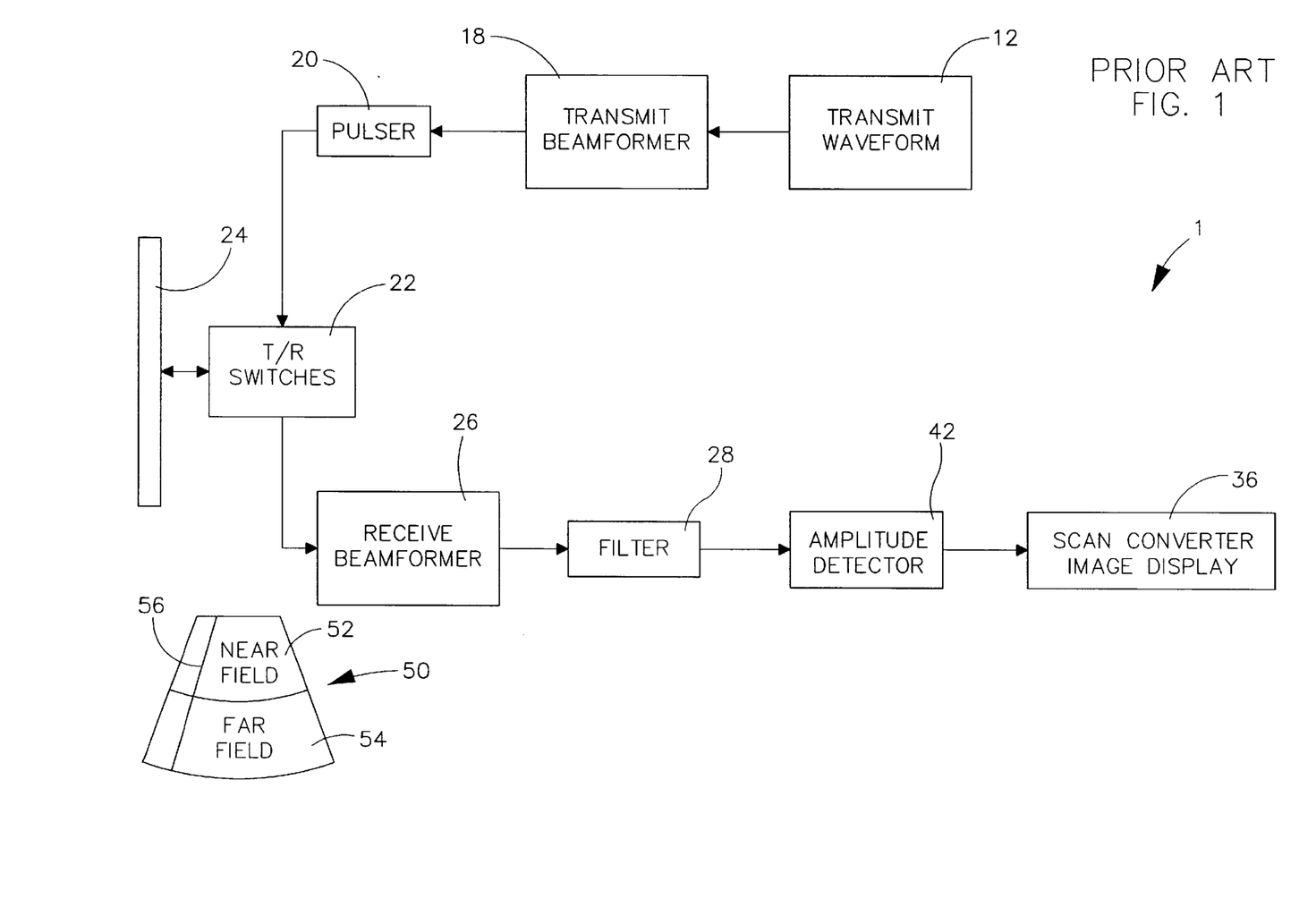
FIG. 1 is a block diagram of the conventional ultrasound imaging system.

Referring now to the drawings in detail wherein like numbers represent like elements throughout, FIG. 1 schematically illustrates a conventional ultrasound imaging system, generally identified 1, The system 1 incorporates a transducer array 24 comprised of a plurality of separately driven transducer elements, each of which produces a burst of ultrasonic energy when energized by a pulser 20 that amplifies the waveform 12. The transmitter 18 drives the transducer array 24 such that the ultrasonic energy is transmitted as a directed focused beam. To accomplish this, proper time delays are imparted to a multiplicity of pulsers 20. Each pulser 20 is coupled to a respective transducer element via transmit/receive (T/R) switches 22. The T/R switches 22 are typically diodes which protect the receive electronics from the high voltages generated by the transmit electronics. The transmit signal causes the diodes to shut off or limit the signal to the receiver 26. The transmit focus time delays are preferably read from a look-up table. By appropriately adjusting the transmit focus time delays in a conventional manner, the ultrasonic beam can be directed and focused at a point.

The echo signals produced by each burst of ultrasonic energy reflect from objects located at successive ranges along the ultrasonic beam. The echo signal is sensed separately by each transducer element in the array 24 and converted to an electrical signal and applied separately to a receiver 26 through a set of T/R switches 22. A sample of the echo signal magnitude at a particular point in time represents the amount of reflection occurring at a specific range. Due to differences in the propagation path between a reflecting point and each transducer element, these echo signals will not be detected simultaneously and their amplitudes will not be equal. Receiver 26 typically amplifies the separate echo signals, imparts the proper time delay to each, and sums them to provide a single echo signal which accurately indicates the total ultrasonic energy reflected from a specific point located at a particular range along the ultrasonic beam. The receive focus time delays are computed in real-time using specialized hardware or read from a look-up table. The output signals of the receiver 26 are then filtered in 28, amplitude detected in 42, scan converted and displayed in 36.

The transmitter 18 and receiver 26 are operated under the control of a scan controller (not shown) that is responsive to commands by a human operator. A complete scan is performed by acquiring a series of echoes in which the transmitter 18 is gated ON momentarily to energize each transducer element, and the subsequent echo signal produced by each transducer element is applied to receiver 26. A transducer element may be actuated to begin reception while another transducer element is still transmitting. Receiver 26 combines the separate echo signals from each transducer element to produce a single echo signal that is used to produce a scan line 56 in focal zone 50 and image on a display monitor 36.

Figure 2:
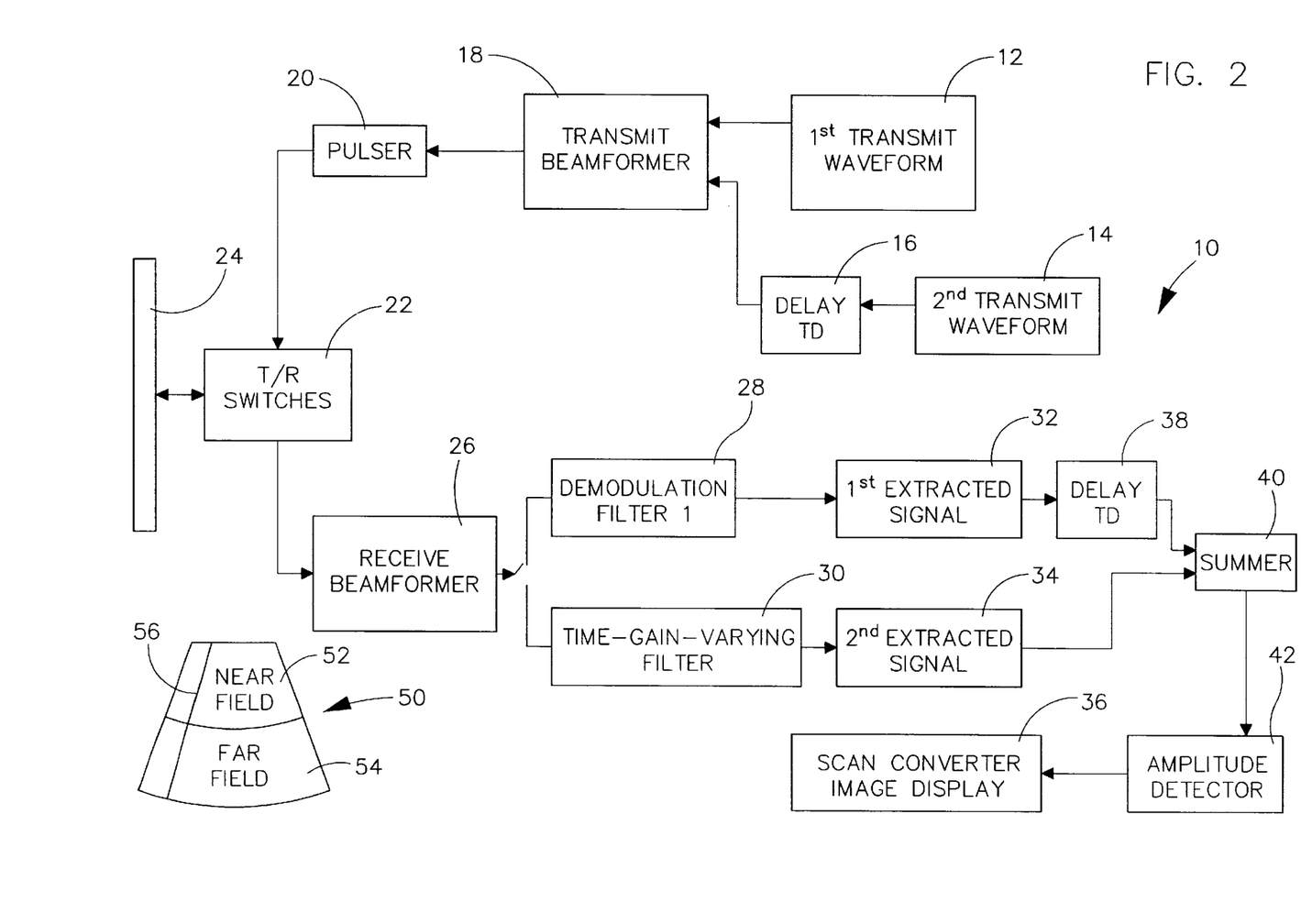
FIG. 2 is a block diagram of the first implementation of an ultrasound imaging system suitable for use with the present invention.
Figure 3:
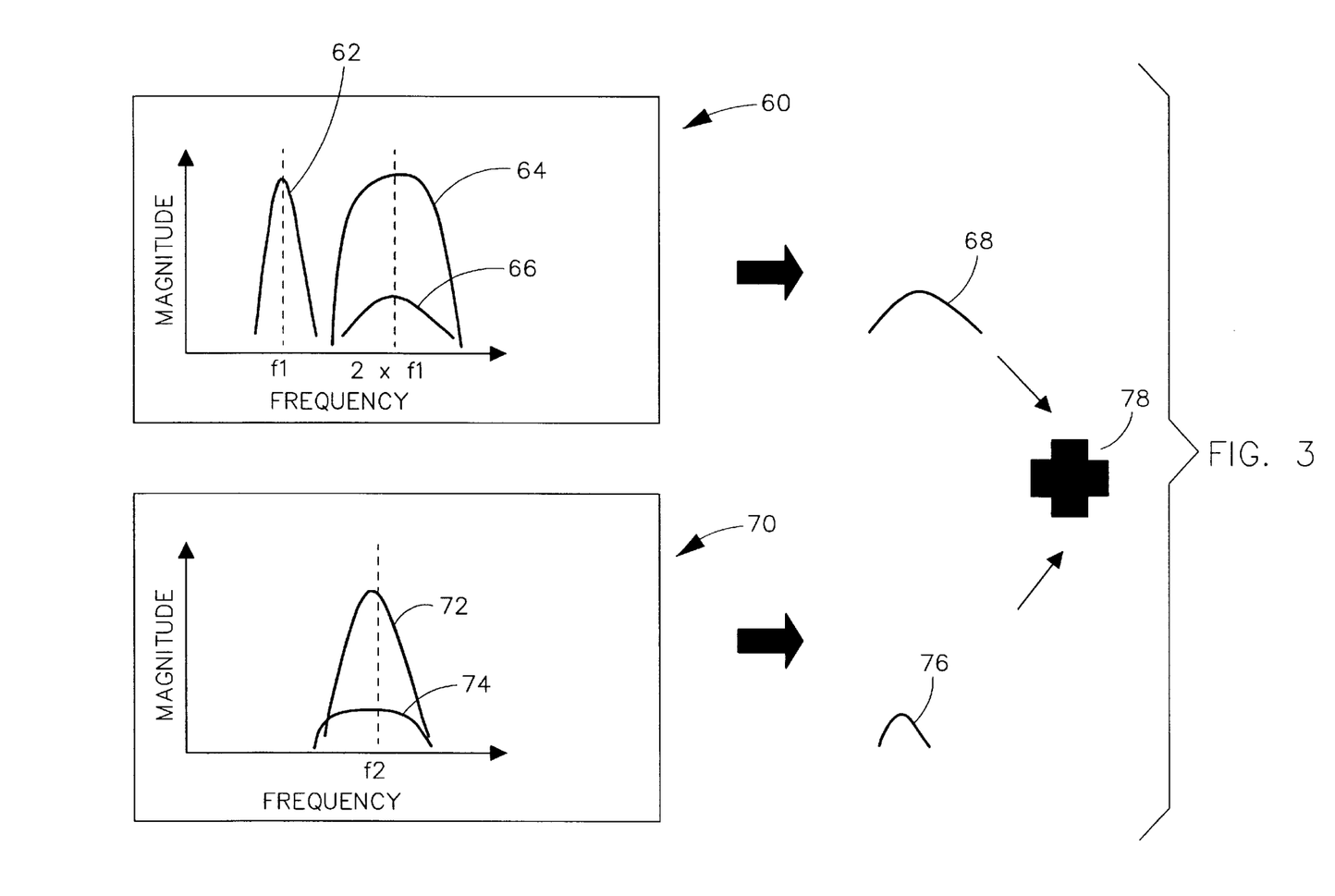
FIG. 3 illustrates a number of graphs showing signal processing for the near field under the first implementation.
Figure 4:
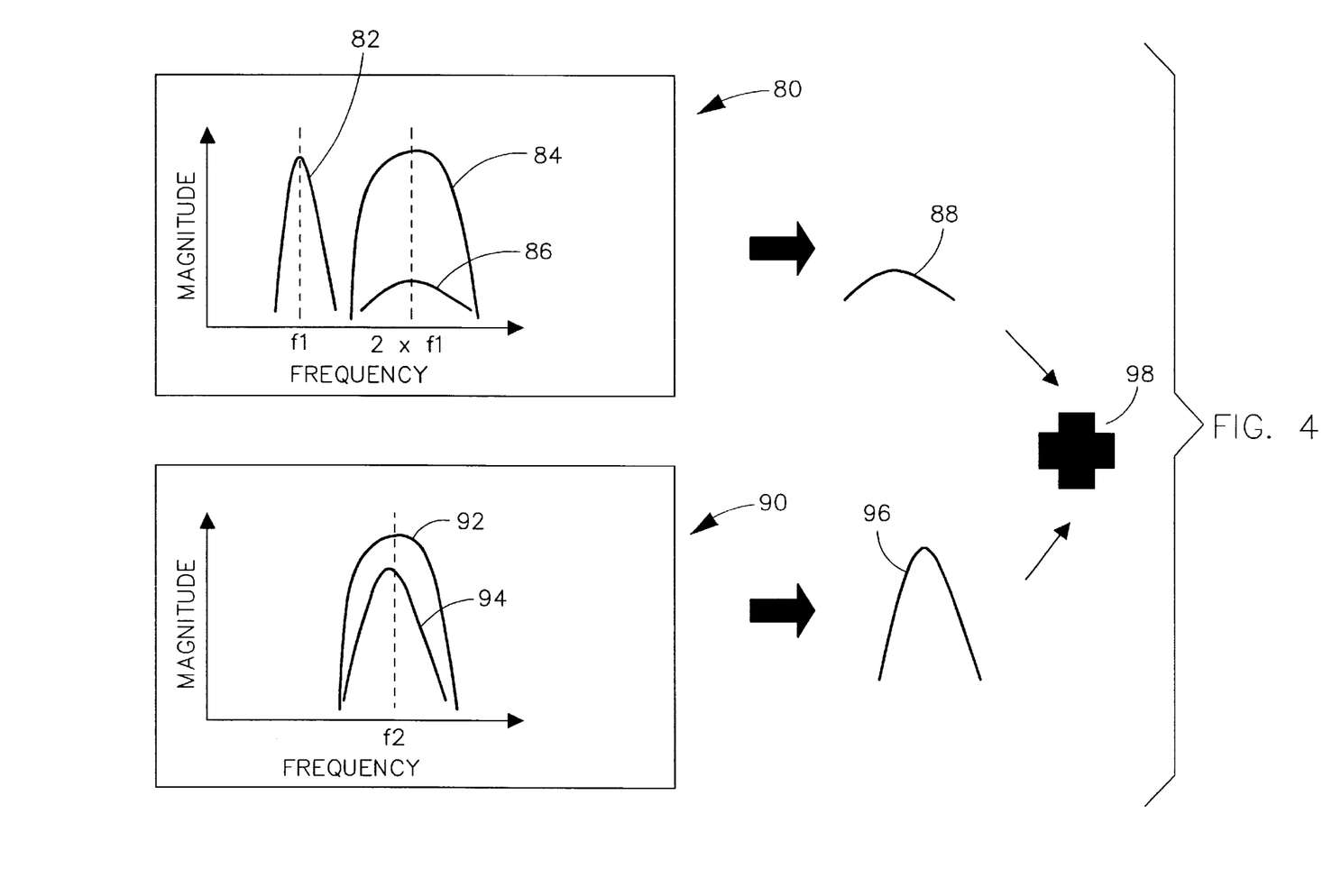
FIG. 4 illustrates a number of graphs showing signal processing for the far field under the first implementation.

FIG. 2 schematically illustrates the preferred embodiment of this invention. More specifically, each scan line 56 associated with a focal zone 50, including the near field 52 or the far field 54, comprises two transmitting events. In the first transmitting event, the pulser 20 uses transmit waveform 12 to energize transducer 24. The corresponding echoes are received by the transducer 24 and beamformed in the receiver 26 in a conventional way. The output signal of the receiver 26 is then filtered in filter 28. The tissue generated harmonic signal 32 is extracted and held in delay line 38. The second transmitting event happens after time delay 16. In this case, the pulser 20 uses transmit waveform 14 to energize the transducer 24. The corresponding echoes are received by the transducer 24 and beamformed in the receiver 26 in a conventional manner. The output signal of the receiver 26 is then filtered in filter 30. The extracted signal 34 is then summed with time delayed signal 32 in the summer 40. The time delay 16 is the time that it takes for the ultrasound wave associated with the first transmitting event to propagate through the tissue and back. The spectra of the transmit waveforms and related signal processing associated with the first and second transmitting events are illustrated in FIGS. 3 and 4. In FIGS. 3 and 4, the first transmitting event is generally identified 60 in the near field 52 and is generally identified 80 in the far field 54. As shown in FIG. 3, the spectrum 62 of the first transmit waveform 12 has center frequency of $f_1$. This spectrum 82 is also shown in FIG. 4. Waveforms 66 and 86 illustrate the spectra of corresponding tissue generated harmonic signals in the near and far field, respectively. These tissue generated harmonic signals 66 and 86 are centered around $2f_1$, and are then filtered by filter 28, resulting in extracted signals 68 in the near field 52 and 88 in the far field 54. In the second transmitting event, generally identified as 70 in the near field 52 and generally identified 90 in the far field 54, the transmitted ultrasound energy is centered around $f_2$ (not shown). The reflected echoes from both near and far field are shown in 72 and 94, respectively. A time-gain-varying filter 30 is used to extract echoes 72 and 94 for the near and far fields 52, 54, respectively. In the near field 52, spectrum 74 of the time-gain-varying filter 30 has lower magnitude, so only a small portion 76 of the echo 72 associated with the second transmitting event is extracted. In the far field 54, spectrum 92 of the time-gain-varying filter 30 has higher magnitude, so most of the echo signal 994 around frequency $f_2$ is extracted 96. See FIG. 3. For the near field, the extracted signals 68 after time delay 38, and 76 are then summed 40 (also shown as signal 78 in FIG. 3). Likewise, in the far field, the extracted signals 88 after time delay 38 and 96 are summed in the summer 40. The output signals of the summer 40 are then amplitude detected 42 and scan converted to form a scan line 56 as shown in FIG. 1. The $f_2$ in the second transmission is designed to be near $2f_1$ as indicated in FIGS. 3 and 4. The extracted signals 68, 88 associated with the first transmitting event reside in the frequency band that has significant overlap with the frequency band associated with the second transmitting event. It should be noted that the time-gain varying filter 30 is a band pass filter whose center frequency can be either a constant or a monotonically decreasing function of time/depth and whose magnitude is a monotonically increasing function of time/depth.

Figure 5:
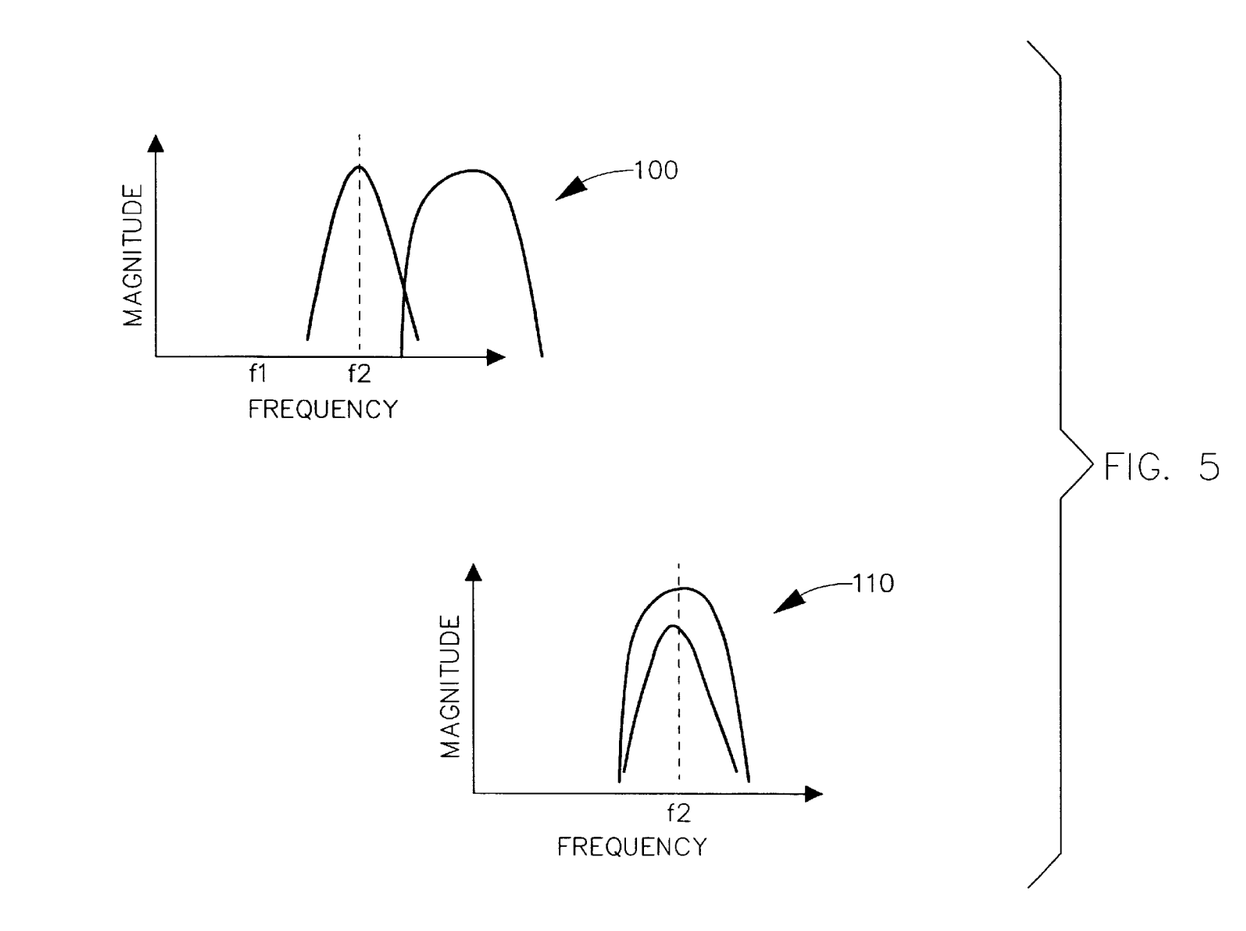
FIG. 5 illustrates a number of graphs showing signals under the time-varying filter mode of the first implementation.

There are several variations to this preferred embodiment. The first transmitting event can comprise multiple firings, e.g. two transmit pulses with their phases differ by 180 degrees. The second transmitting event can comprise multiple firings, e.g. two Golay coded transmit pulses as described in U.S. Pat. No. 6,146,328. The time-gain-varying filter 30 can be replaced with a time-varying filter in which the magnitude of the filter 30 is a constant for the entire time/depth, but the center frequency of this band-pass filter decreases with the time/depth. This is shown in FIG. 5. where waveform 100 is the spectrum of the filter at a shallow depth, while waveform 110 is the spectrum of the same filter at a deeper depth.

Figure 6:
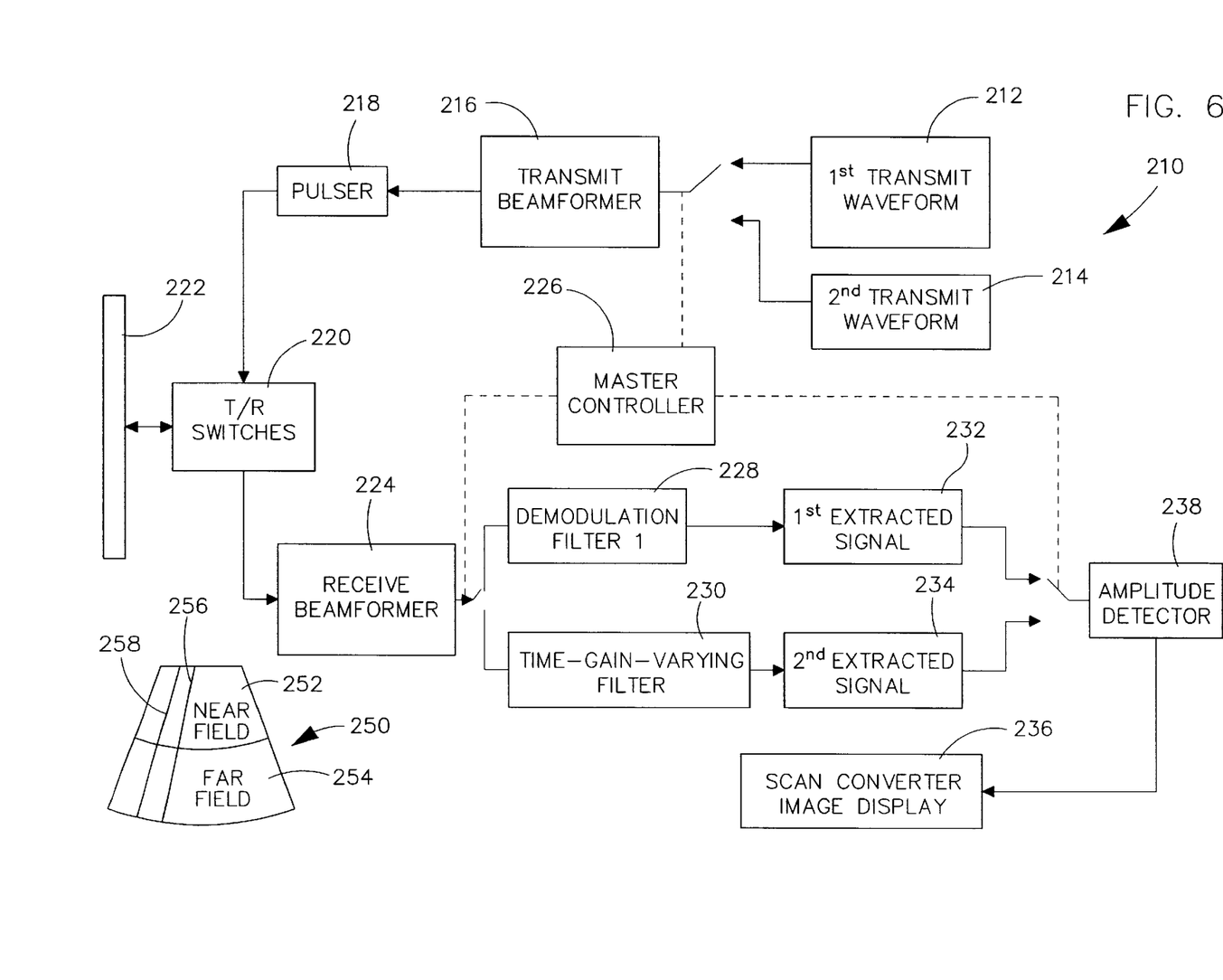
FIG. 6 is a block diagram of a second implementation of an ultrasound imaging system suitable for use with the present invention.

Referring now to the other embodiment, FIG. 6 illustrates a schematic diagram, generally identified 210, of this embodiment. More specifically, the first transmitting event is used for the even scan lines 256 and the second transmitting event is used for the odd scan lines 258. As before, the focal zone 250 includes the near field 252 and the far field 254. Unlike the preferred embodiment, however, the extracted signals 232, 234 from the first and second transmitting events are amplitude detected 238 separately and scan converted 236 according to their scan line position in the image. As shown, the first transmit waveform 212 and the second transmit waveform 214 are input controlled to the transmit beamformer 216 by means of a master controller 226. The master controller 216 also controls output from the receive beamformer 224 and input to the amplitude detector 238. In other respects, this implementation 210 is similar to the first in that pulsers 218, T/R switches 220 and an array 222 of transducers are utilized. Also, a filter 228 is used for the first extracted signal 232 and a time-gain-varying filter 230 is used for the second extracted signal 234.

Figure 7:
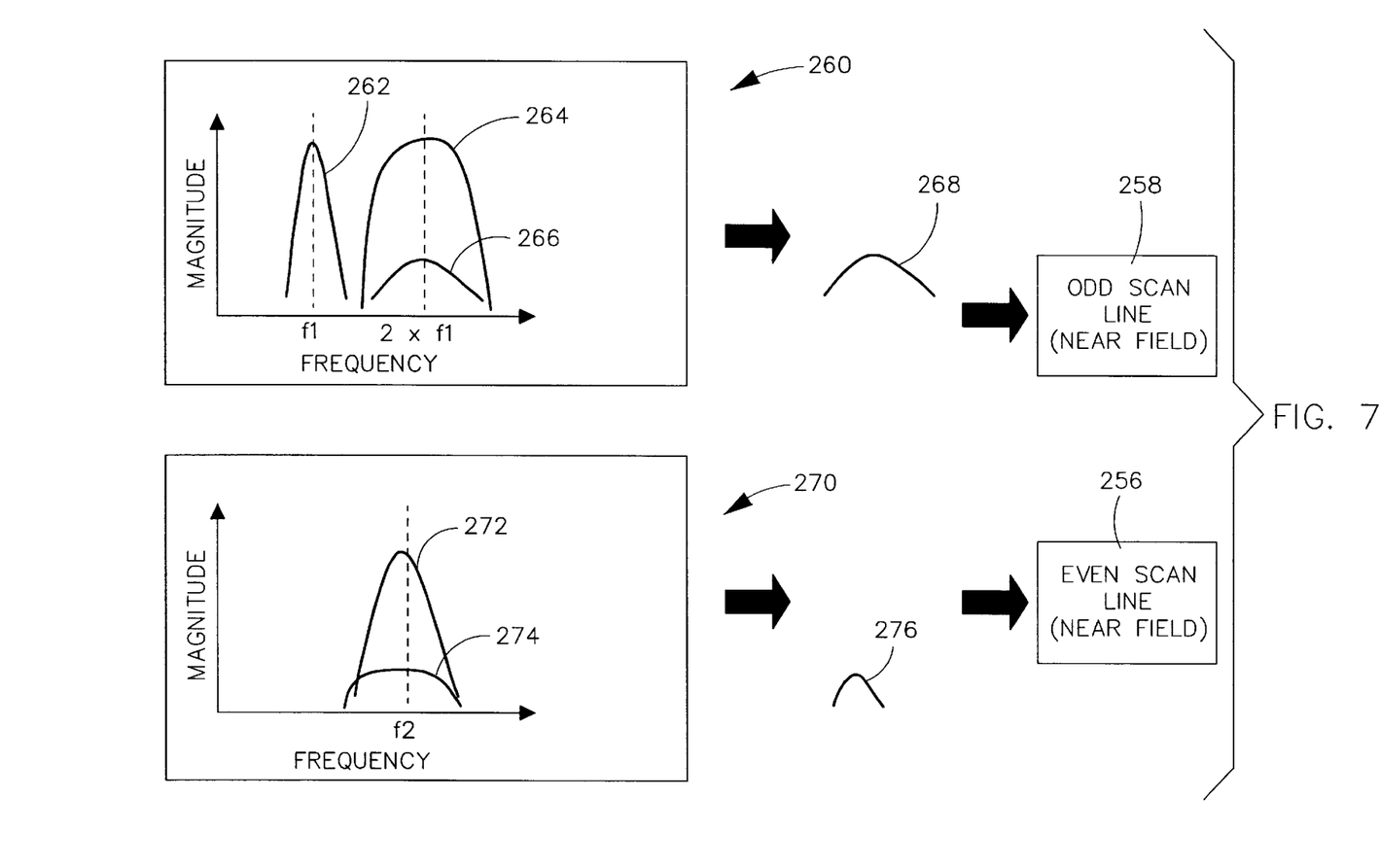
FIG. 7 illustrates a number of graphs showing signal processing for the near field under the second implementation.
Figure 8:
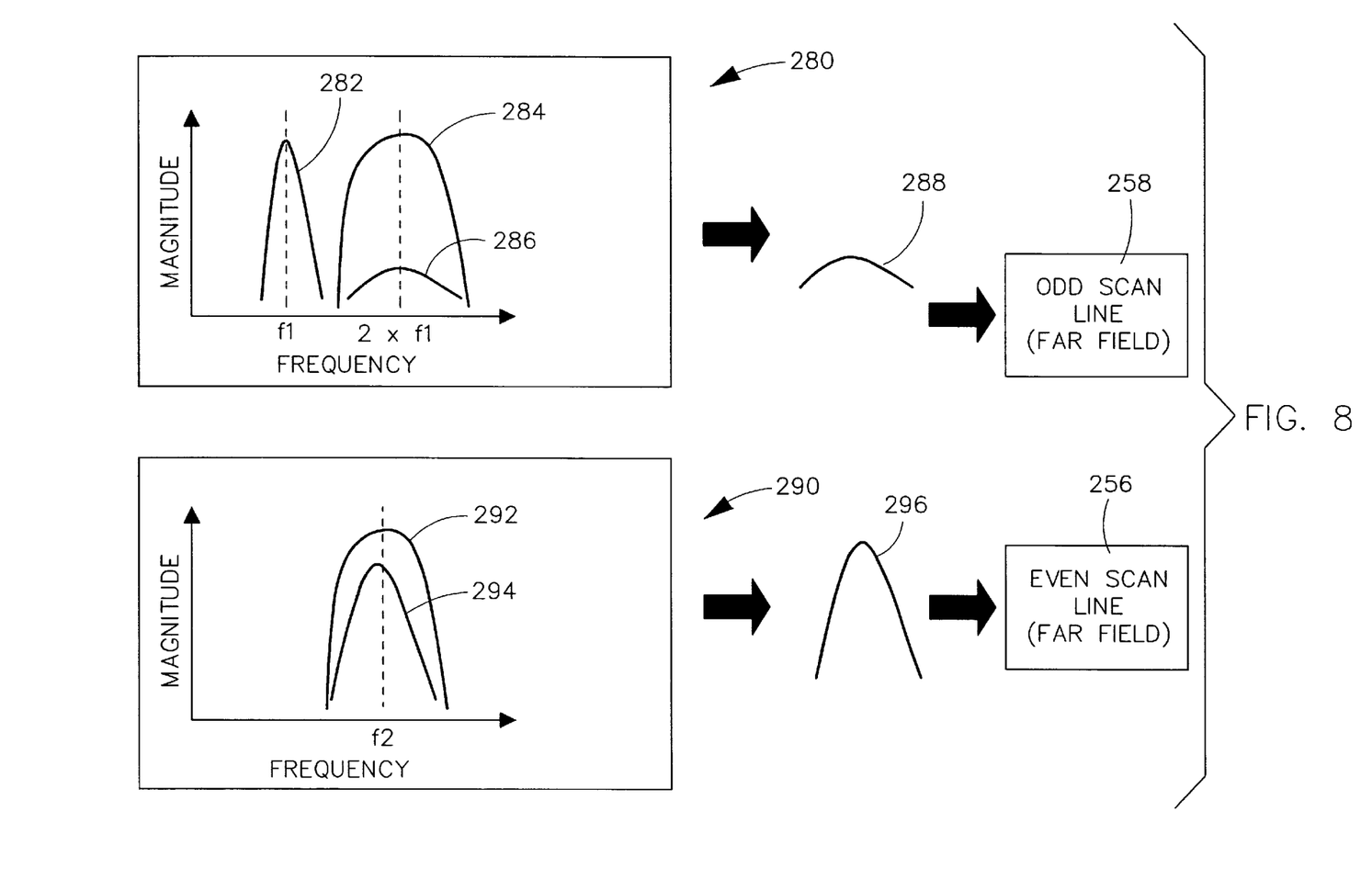
FIG. 8 illustrates a number of graphs showing signal processing for the far field under the second implementation.

FIG. 7 shows the signal processing, generally identified 260, 270, used for the near field image, and FIG. 7 illustrates the signal processing, generally identified 280, 290, used for the far field image. More specifically, the first transmitting event is generally identified 260 in the near field 252 and is generally identified 280 in the far field 254. As shown in FIGS. 6 and 7, the spectrum 262 of the first transmit waveform 212 is illustrated which has center frequency of $f_1$. This spectrum 282 is also illustrated in FIG. 8. Waveforms 266 and 286 illustrate the spectra of corresponding tissue generated harmonic signals in the near and far field, respectively. These tissue generated harmonic signals 266 and 286 are centered around $2f_1$, and are then filtered by filter 228, resulting in extracted signals 268 in the near field and 288 in the far field. The spectrum of the filter 228 is shown as 264 and 284 in FIGS. 7 and 8, respectively. The extracted signals 268, 288 are then amplitude detected 238 and scan converted 236 for the odd scan line 258. In the second transmitting event, generally identified as 270 in the near field 252 and generally identified 290 in the far field 254, the transmitted ultrasound energy is centered around $f_2$ (not shown). The reflected echoes from both near and far field are shown in 272 and 294, respectively. A time-gain-varying filter 230 is used to extract echoes 272 and 294 for the near and far fields 252, 254, respectively. In the near field 252, spectrum of the time-gain-varying filter 230 shown as 274 has lower magnitude, so only a small portion of the echo 272 associated with the second transmitting event is extracted shown as 276. See FIG. 7. In the far field 254, spectrum 292 of the time-gain-varying filter 230 has higher magnitude, so most of the echo signal 294 around frequency $f_2$ is extracted 296. See FIG. 8. The extracted signals 276, 296 are then amplitude detected 238 and scan converted for the even scan line 256. The $f_2$ in the second transmission is designed to be near $2f_1$, as indicated in FIGS. 7 and 8. It should be stressed that the three variations mentioned in the preferred embodiment 10 also apply to this embodiment 210.

Parts List

1 Prior art ultrasound imaging system
10 Preferred embodiment of ultrasound imaging system
11 First transmit wave form
14 Second transmit wave form
15 Time delay
18 Transmit beamformer
20 Pulser
22 Transmit/receive switches
24 Transducer array
26. Receive beamformer
28 Demodulation filter
30. Time-gain-varying filter
32 First extracted signal
34 Second extracted signal
36 Scan converter image display
38 Time delay
40 Summer
42 Amplitude detector
50 Focal zone
52 Near field
54 Far field
56 Scan line
60 First transmitting event in the near field
62 First transmit wave form at frequency $f_1$
64 First demodulation filter
66 Tissue generated harmonic signal centered at $2f_1$
68 Extracted harmonic signal from near field
70 Second transmitting event in the near field
72 Second transmit and receive signal in near field
74 Time-gain-varying filter in the near field
76 Second extracted signal in near field
78 Near field image
80 First transmitting event in the far field
82 First transmit wave form in far field
84 First demodulation filter
86 Tissue generated harmonic signal
88 First extracted signal for far field
90 Second transmitting event in the far field
92 Time-gain-varying filter
94 Echo in the far field
96 Second extracted signal
98 Far field image
100 Spectrum of filter at shallow depth
110 Spectrum of filter at deeper depth
210 Alternative embodiment of ultrasound imaging system
212 First transmit wave form
214 Second transmit wave form
216 Transmit beamformer
218 Pulser
220 Transmit/receive switches
222 Transducer array
224 Receive beamformer
226 Master controller
228 Demodulation filter
230 Time-gain-varying filter 232 First extracted signal
234 Second extracted signal
236 Scan converter image display
238 Amplitude detector
250 Focal zone
252 Near field
254 Far field
256 Even scan line
258 Odd scan line
260 First transmitting event in the near field
262 First transmit waveform
264 First demodulation filter
266 Tissue generated harmonic signal
268 First extracted signal for near field
270 Second transmitting event in near field
272 Second transmit and receive signal
274 Second demodulation filter
276 Second extracted signal for near field
280 First transmitting event in the far field
282 First transmit waveform
284 First demodulation filter
286 Tissue generated harmonic signal
288 First extracted signal for far field
290 Second transmitting event in the far field
292 Second demodulation filter
294 Second transmit and receive signal
296 Second extracted signal for far field

What is claimed is:

1. A method for harmonic ultrasound imaging using multiple transmissions comprising the steps of
providing a first transmitting event,
extracting a tissue generated harmonic signal associated with the first transmitting event in the near field,
providing a second transmitting event, and
extracting a fundamental echo signal associated with the second transmitting event in the far field,
wherein composite imaging of the extracted signals results in similar speckle size across the entire image.

2. The ultrasound imaging method of claim 1 wherein the tissue generated harmonic signal has a frequency band centered on $2f_1$ and the fundamental echo signal from the second transmitting event has a frequency band centered on $f_2$ wherein $f_2$ in the second transmitting event is close to $2f_1$.

3. The ultrasound imaging method of claim 2 wherein there is a significant overlap in frequency band between signals extracted from the first transmitting event and signals extracted from the second transmitting event.

4. A method for harmonic ultrasound imaging comprising the steps of
providing a first transmitting event in the near field and in the far field, the ultrasonic energy being transmitted by means of a first transmit wave form at the center frequency of $f_1$,
receiving the corresponding echo from the first transmitting event,
extracting the tissue generated harmonic signal that is centered around $2f_1$ for the near field and the far field,
generating a second transmitting event in the near field and the far field at the center frequency of $f_2$,
using a time-gain-varying filter to extract signals for the near and far fields,
wherein the extracted signals associated with the first transmitting event reside in a frequency band that has significant overlap with the frequency band associated with the second transmitting event.

5. The method for ultrasound imaging of claim 4 wherein the time-gain-varying filter is a band pass filter whose center frequency can be either a constant or a monotonically decreasing of time/depth and whose magnitude is a monotonically increasing function of time/depth.

6. The ultrasound imaging method of claim 5 wherein the first transmitting event comprises a plurality of phase-shifted multiple firings.

7. The ultrasound imaging method of claim 5 wherein the second transmitting event comprises multiple firings.

8. The ultrasound imaging method of claim 5 wherein the time-gain-varying filter is replaced by a time-varying filter and the time-varying filter is a constant.

9. A method for harmonic ultrasound imaging using multiple transmissions comprising the steps of
providing a first transmitting event used for even scan lines in the near field and in the far field,
extracting a first echo signal associated with the first transmitting event,
filtering the first echo signal with a demodulation filter,
providing a second transmitting event used for odd scan lines in the near field and in the far field,
extracting a second echo signal associated with the second transmitting event,
filtering the second echo signal with a time-gain-varying filter, and
amplitude detecting and scan converting the extracted echo signals,
wherein composite imaging of the extracted signals results in similar speckle size across the entire image.

10. The ultrasound imaging method of claim 9 wherein the first transmitting event comprises a plurality of phase-shifted multiple firings.

11. The ultrasound imaging method of claim 9 wherein the second transmitting event comprises multiple firings.

12. The ultrasound imaging method of claim 9 wherein the time-gain-varying filter is replaced by a time-varying filter in which the magnitude of the time-varying filter is a constant for the entire time/depth, but the center frequency of this band-pass filter decreases with the time/depth.

13. An ultrasound imaging device that uses multiple transmissions to create the scan line of an ultrasound image which comprises
means for providing a first transmitting event,
means for extracting a tissue generated harmonic signal associated with the first transmitting event in the near field,
means for providing a second transmitting event, and
means for extracting a fundamental echo signal associated with the second transmitting event in the far field,
wherein the composite imaging of the extracted signals results in similar speckle size across the entire image.

14. The ultrasound imaging device of claim 13 wherein the tissue generated harmonic signal has a frequency band centered on $2f_1$ and the fundamental echo signal from the second transmitting event has a frequency band centered on $f_2$ wherein $f_2$ in the second transmitting event is close to $2f_1$.

15. The ultrasound imaging device of claim 13 wherein there is a significant overlap in frequency band between signals extracted from the first transmitting event and signals extracted from the second transmitting event.

16. An ultrasound imaging device which comprises means for providing a first transmitting event in the near field and in the far field, the ultrasonic energy being transmitted by means of a first transmit wave form at the center frequency of $f_1$, means for receiving the corresponding echo from the first transmitting event, means for extracting the tissue generated harmonic signal that is centered around $2f_1$ for the near field and the far field, means for generating a second transmitting event in the near field and the far field at the center frequency of $f_2$, a time-gain-varying filter to extract signals for the near and far fields, wherein the extracted signals associated with the first transmitting event reside in a frequency band that has significant overlap with the frequency band associated with the second transmitting event.

17. The ultrasound imaging device of claim 16 wherein the time-gain-varying filter is a band pass filter whose center frequency can be either a constant or a monotonically decreasing of time/depth and whose magnitude is a monotonically increasing function of time/depth.

18. The ultrasound imaging device of claim 16 wherein the first transmitting event means comprises a means for providing a plurality of phase-shifted multiple firings.

19. The ultrasound imaging device of claim 16 wherein the second transmitting event means comprises means for providing multiple firings.

20. The ultrasound imaging device of claim 16 wherein the time-gain-varying filter is replaced by a time-varying filter in which the magnitude of the filter 30 is a constant for the entire time/depth, but the center frequency of this band-pass filter decreases with the time/depth.

21. An ultrasound imaging device which comprises means for providing a first transmitting event used for even scan lines in the near field and in the far field, means for extracting a first echo signal associated with the first transmitting event, means for filtering the first echo signal with a demodulation filter, means for providing a second transmitting event used for odd scan lines in the near field and in the far field, means for extracting a second echo signal associated with the second transmitting event, a time-gain-varying filter for filtering the second echo signal, and means for amplitude detecting and scan converting the extracted echo signals, wherein composite imaging of the extracted signals results in similar speckle size across the entire image.

22. The ultrasound imaging device of claim 21 wherein the first transmitting event providing means includes means for providing a plurality of phase-shifted multiple firings.

23. The ultrasound imaging device of claim 21 wherein the second transmitting event providing means includes means for providing multiple firings.

24. The ultrasound imaging device of claim 21 wherein the time-gain-varying filter is replaced by a time-varying filter in which the magnitude of the time-varying filter is a constant for the entire time/depth, but the center frequency of this band-pass filter decreases with the time/depth.

* * * * *